United States Patent [19]

Bowers et al.

[11] Patent Number: 5,663,146
[45] Date of Patent: Sep. 2, 1997

[54] POLYPEPTIDE ANALOGUES HAVING GROWTH HORMONE RELEASING ACTIVITY

[75] Inventors: Cyril Y. Bowers; David Coy, both of New Orleans, La.

[73] Assignee: Administrators of the Tulane Educational Fund, New Orleans, La.

[21] Appl. No.: 748,350

[22] Filed: Aug. 22, 1991

[51] Int. Cl.⁶ ..................................................... A61K 38/00
[52] U.S. Cl. ........................... 514/16; 514/17; 530/328; 530/329
[58] Field of Search ................. 514/16, 17; 530/328–329

[56] References Cited

U.S. PATENT DOCUMENTS

| | | | |
|---|---|---|---|
| 4,223,019 | 9/1980 | Momany | 514/17 |
| 4,223,020 | 9/1980 | Momany | 514/18 |
| 4,223,021 | 9/1980 | Momany | 514/17 |
| 4,224,316 | 9/1980 | Momany | 514/17 |
| 4,226,857 | 10/1980 | Momany | 514/17 |
| 4,228,155 | 10/1980 | Momany | 514/17 |
| 4,228,156 | 10/1980 | Momany . | |
| 4,228,157 | 10/1980 | Momany . | |
| 4,228,158 | 10/1980 | Momany . | |
| 4,410,512 | 10/1983 | Bowers . | |
| 4,410,513 | 10/1983 | Momany . | |

FOREIGN PATENT DOCUMENTS

| | | |
|---|---|---|
| 8907110 | 8/1989 | WIPO . |
| 8907111 | 8/1989 | WIPO . |
| 8910933 | 11/1989 | WIPO . |

*Primary Examiner*—Cecilia J. Tsang
*Assistant Examiner*—S. G. Marshall
*Attorney, Agent, or Firm*—Ronald I. Eisenstein

[57] ABSTRACT

Novel peptides of the formula $A_1$-$A_2$-Ala-Trp-DPhe-$A_5$ are disclosed which promote the release of growth hormone when administered to animals. These peptides can be used therapeutically.

35 Claims, No Drawings

POLYPEPTIDE ANALOGUES HAVING GROWTH HORMONE RELEASING ACTIVITY

This invention relates to novel polypeptide compounds which promote the release of growth hormone when administered to animals, preferably humans. In another aspect, this invention relates to methods for promoting the release and elevation of growth hormone levels in animals by administration of specified growth hormone releasing polypeptide compounds thereto.

BACKGROUND OF THE INVENTION

The elevation of growth hormone (GH) levels in animals, e.g., mammals including humans, upon administration of GH-releasing compounds can lead to enhanced body weight and to enhanced milk production if sufficiently elevated GH levels occur upon administration. Further, it is known that the elevation of growth hormone levels in mammals and humans can be accomplished by application of known growth hormone releasing agents, such as the naturally occurring growth hormone releasing hormones.

The elevation of growth hormone levels in mammals can also be accomplished by application of growth hormone releasing peptides, some of which have been previously described, for example, in U.S. Pat. No. 4,223,019, U.S. Pat. No. 4,223,020, U.S. Pat. No. 4,223,021, U.S. Pat. No. 4,224,316, U.S. Pat. No. 4,226,857, U.S. Pat. No. 4,228,155, U.S. Pat. No. 4,228,156, U.S. Pat. No. 4,228,157, U.S. Pat. No. 4,228,158, U.S. Pat. No. 4,410,512, U.S. Pat. No. 4,410,513.

Antibodies to the endogenous growth hormone release inhibitor, somatostatin (SRIF) have also been used to cause elevated GH levels. In this latter example, growth hormone levels are elevated by removing the endogenous GH-release inhibitor (SRIF) before it reaches the pituitary, where it inhibits the release of GH.

Each of these methods for promoting the elevation of growth hormone levels involve materials which are expensive to synthesize and/or isolate in sufficient purity for administration to a target animal. Short chain, low molecular weight, relatively simple polypeptides which are relatively inexpensive to prepare and have the ability to promote the release of growth hormone would be desirable because they should be readily and inexpensively prepared, easily modified chemically and/or physically, as well as easily purified and formulated; and they should have excellent transport properties.

Although some short chain polypeptides which can promote the release and elevation of growth hormone levels in the blood are known, it is important to be able to tailor polypeptides for a variety of reasons, such as delivery, bioabsorbance, increased retention time, etc. However, amino acid changes at certain positions can have dramatic effects on the ability of short chain peptide to promote the release of a growth hormone.

It would be desirable to have different short chain polypeptides which can promote the release and elevation of growth hormone levels in the blood of animals, particularly in humans. It would also be useful to be able to use such polypeptides to promote the release and/or elevation of growth hormone levels in the blood of animals and humans.

It would also be desirable to provide methods for promoting the release and/or elevation of growth hormone levels in the blood of animals using such short chain polypeptides.

SUMMARY OF THE INVENTION

The polypeptides are defined by the following formula:

$A_1$-$A_2$-Ala-Trp-DPhe-$A_5$, where $A_1$ is Gly, DAla, β-Ala, His, Ser, Met, Pro, Sar, Ava, Aib, a N-lower alkylaminocarboxylic acid, a N,N-bis-lower alkyl amino-carboxylic acid or a lower alkyl aminocarboxylic acid, wherein the lower alkyl group comprises 2 to about 10 straight-chain carbon atoms. $A_1$ is preferably DAla.

$A_2$ is DTrp,$D^\beta$Nal, D-4-Y-Phe-or 5-Y-D-Trp, wherein Y is OH, Cl, Br, F or H. More preferably, $A_2$ is $D^\beta$Nal.

$A_5$ is $A_3$-$A_4$-$A_{5'}$, $A_3$-$A_{5'}$, $A_4$-$A_{5'}$ or $A_{5'}$. Preferably $A_5$ is $A_{5'}$. $A_3$ is Ala, Gly, DAla, Pro or desAla. $A_4$ is Ala, Gly, DAla, Pro, a linear lower alkyl aminocaboxylic acid, or desAla. $A_{5'}$ is Lys(ξ-$R_1$, $R_2$)-Z, Orn(δ-$R_1$, $R_2$)-Z, NH(CH$_2$)$_x$N($R_3$, $R_4$). $A_{5'}$ can also be Lys-Z, Orn-Z or Arg-Z when $A_1$ is not His. $R_1$ is a linear lower alkyl group or H atom. $R_2$ is a linear lower alkyl group or H atom. When $R_1$ is H, $R_2$ is not H; similarly when $R_2$ is H, $R_1$ is not H. $R_3$ is a linear lower alkyl groups or H atom. $R_4$ is a linear lower alkyl group or H atom. The lower alkyl group comprises 2 to about 10 straight-chain carbon atoms. Z is NH(linear lower alkyl groups, N(linear lower alkyl group)$_2$, O-(linear lower alkyl group), NH$_2$ or OH, wherein the linear lower alkyl group is as defined above. x is 2 through 15. And organic or inorganic addition salts of any of said polypeptides.

DETAILED DESCRIPTION OF THE INVENTION

We have discovered several novel short chain polypeptides which promote the release and elevation of growth hormone levels in the blood of animals. The polypeptides are defined by the following formula:

$A_1$-$A_2$-Ala-Trp-DPhe-$A_5$, where $A_1$ is Gly, DAla, β-Ala, His, Ser, Met, Pro, Sar, Ava, Aib, imidazole acetic acid, a N-lower alkyl aminocarboxylic acid, a N,N-bis-lower alkyl amino-carboxylic acid or a lower alkyl aminocarboxylic acid, wherein the lower alkyl group comprises 2 to about 10 straight-chain carbon atoms. Preferably, the lower alkyl group is 2 to 6 straight-chain carbon atoms. The lower alkyl group can be substituted or unsubstituted. Preferred substituents are O, N or Si. Preferably, the lower alkyl group is unsubstituted. Preferably, $A_1$ is Gly, DAla or His. Still more preferably $A_1$ is His or DAla. $A_1$ is most preferably DAla.

$A_2$ is DTrp,$D^\beta$Nal, D-4-Y-Phe-or 5-Y-D-Trp, wherein Y is OH, Cl, Br, F or H. Preferably, $A_2$ is $D^\beta$Nal, D-4-Y-Phe or 5-Y-D-Trp. More preferably, $A_2$ is $D^\beta$Nal. Y is preferably OH or H.

$A_5$ is $A_3$-$A_4$-$A_{5'}$, $A_3$-$A_{5'}$, $A_4$-$A_{5'}$, or $A_{5'}$. Preferably $A_5$ is $A_{5'}$. $A_3$ is Ala, Gly, DAla, Pro or desAla. $A_4$ is Ala, Gly, DAla, Pro, a linear lower alkyl aminocaboxylic acid, or desAla. $A_{5'}$ is Lys(ξ-$R_1$,$R_2$)-Z, Orn(δ-$R_1$, $R_2$)-Z, LArg (g-$R_5$-$R_6$) NH(CH$_2$)$_x$N($R_3$, $R_4$). $A_{5'}$ can also be Lys-Z, Orn-Z or Arg-Z when $A_1$ is not His. $R_1$ is a linear lower alkyl group or H atom. $R_2$ is a linear lower alkyl group or H atom. When $R_1$ is H, $R_2$ is not H; similarly when $R_2$ is H, $R_1$ is not H. $R_3$ is a linear lower alkyl groups or H atom. $R_4$ is a linear lower alkyl group or H atom. $R_5$ and $R_6$ are linear lower alkyl groups. The lower alkyl group comprises 2 to about 10 straight-chain carbon atoms. Preferably, the lower alkyl group is 2 to 6 straight-chain carbon atoms. The lower alkyl group can be substituted or unsubstituted. Preferred substituents can be O, N or Si. Preferably, the lower alkyl group is unsubstituted. g is guanidino. Z is NH(linear lower alkyl group), N(linear lower alkyl group)$_2$, O-(linear lower alkyl group), NH$_2$ or OH, wherein the linear lower alkyl group is as defined above. x is 2 through 15. x is preferably 2 through 6. $A_5$, is preferably Lys-$NH_2$. And organic or inorganic addition salts of any of said polypeptides.

The amino acid residue abbreviations used are in accordance with standard peptide nomenclature:

Gly=Glycine
Tyr=L-Tyrosine
Ile=L-Isoleucine
Glu=L-Glutamic Acid
Thr=L-Threonine
Phe=L-Phenylalanine
Ala=L-Alanine
Lys=L-Lysine
Asp=L-Aspartic Acid
Cys=L-Cysteine
Arg=L-Arginine
Ava=Aminovaleric acid
Aib=Aminoisobutyric acid
Gln=L-Glutamine
Pro=L-Proline
Leu=L-Leucine
Met=L-Methionine
Ser=L-Serine
Asn=L-Asparagine
His=L-Histidine
Trp=L-Tryptophan
Val=L-Valine
DOPA=3,4-Dihydroxyphenylalanine
Met(O)=Methionine Sulfoxide
Abu=α-Aminobutyric Acid
iLys=$N^\epsilon$-Isopropyl-L-Lysine
4-Abu=4-Aminobutyric Acid
Orn=L-Ornithine
$D^\alpha$Nal=α-Naphthyl-D-Alanine
$D^\beta$Nal=β-Naphthyl-D-Alanine
Sar=Sarcosine
LArg=homoArgninine All three letter amino acid abbreviations preceded by a "D" indicated the D-configuration of the amino acid residue, and glycine is considered to be included in the term "naturally occurring L-amino acids."

The flexibility associated with the choice of basic, neutral or acidic amino acid residues that can be used for amino acids $A_1$, $A_2$, $A_3$ $A_4$ and $A_5$ provides a great deal of control over the physiochemical properties of the desired peptide. Such flexibility provides important advantages for the formulation and delivery of the desired peptide to any given species. Also, these changes may improve oral absorption as well as metabolism and excretion of the peptides. The moieties of $R_1$, $R_2$, $R_3$, $R_4$ and Z can be varied as well, thereby providing added control over the physiochemical properties of the desired compound. Consequently, one can obtain enhanced delivery of a peptide to a particular receptor and in particular species.

Preferred growth hormone releasing compounds employed in the practice of the present invention are:

$A_1$-$A_2$-Ala-Trp-DPhe-$A_5$, or organic or inorganic addition salts of any polypeptides; where $A_1$, $A_2$ and $A_5$, are as defined above.

In a preferred embodiment, the growth hormone releasing peptide employed in the practice of the present invention has the formula:

DAla-$A_2$-Ala-Trp-DPhe-$A_5$, and organic or inorganic addition salts thereof. Preferred members of this group of compounds have the formula:

DAla-$D^\beta$Nal-Ala-Trp-DPhe-LysNH$_2$

DAla-$D^\beta$Nal-Ala-Trp-DPhe-Lys(ε-iPr)NH$_2$

DAla-DTrp-Ala-Trp-DPhe-LysNH$_2$

DAla-$D^\beta$Nal-Ala-Trp-DPhe-NH(CH$_2$)$_5$NH$_2$, and

NH$_2$(CH$_2$)$_5$CO-$D^\beta$-Nal-Ala-Trp-D-Phe-NH(CH$_2$)$_5$NH$_2$ as well as organic or inorganic addition salts thereof.

These compounds are presently the most preferred because these shorter chain polypeptides are less expensive to synthesize, and these specific compounds have been shown to have a high level of potency at promoting the increase in serum growth hormone levels.

These compounds are typically easy to synthesize, have efficacy at promoting an increase in serum growth hormone levels, and are desirable for commercial scale production and utilization. In addition, these compounds maybe advantageous in having physiochemical properties which are desirable for the efficient delivery of such polypeptide compounds to a wide variety of animal species because of the flexibility made possible by the various substitutions at numerous positions of the polypeptide compounds, by selecting the polar, neutral or non-polar nature of the C-terminal and center portions of these polypeptide compounds so as to be compatible with the desired method of delivery is oral, nasal, continuous delivery utilizing special chemical/mechanical methods of delivery.

These peptides can be used therapeutically for any use for which growth hormone can be used such as treating hypothalamic pituitary dwarfism, osteoporosis, burns, and renal failure for acute use, for non-union bone fracture, and to promote wound healing. Additionally, it can be used to promote recovery from surgery, and acute/chronic debilitating medical illnesses. Beneficial anabolic effects result on skin, muscle and bone in relation to the aging process with a concomitant decrease in body fat. Treatment of cancer patients by these peptides is also included, for example, prevention and/or reduction of cachexia in cancer patients. These therapeutic uses are accomplished by using a therapeutically effective amount of the peptide. Such an amount is that needed to promote the release of serum growth hormone levels as discussed, infra.

The compounds of this invention may also be used to enhance blood GH levels in animals; enhance milk production in cows; enhance body growth in animals such as mammals (e.g., humans, sheep, bovines, and swine), as well as fish, fowl, other vertebrates and crustaceans; and increase wool and/or fur production in mammals. The amount of body growth is dependent upon the sex and age of the animal species, quantity and identity of the growth hormone releasing compound being administered, route of administration, and the like. Also, the compounds of this invention increase serum GH in humans; enhance body growth in short stature children; decrease body fat and improve protein metabolism in select children; improve protein metabolism of the skin, muscle, bone while decreasing body fat of the elderly, particularly when GH deficiency is present.

These peptides are also useful for improving serum lipid pattern in humans by decreasing in the serum the amount of serum cholesterol and low density lipoprotein and increasing in the serum the amount of the high density lipoprotein.

The novel polypeptide compounds of this invention can be synthesized according to the usual methods of solution and solid phase peptide chemistry, or by classical methods known in the art.

For the peptide amides, the solid-phase synthesis is preferred commenced from the C-terminal end of the peptide. A suitable starting material can be prepared, for instance, by attaching the required protected alpha-amino acid to a chloromethylated resin, a hydroxymethyl resin, a benzhydrylamine (BHA) resin, or a para-methyl-benzylhydrylamine (p-Me-BHA) resin. One such chloromethyl resin is sold under the tradename BIOBEADS SX-1 by Bio Rad Laboratories, Richmond, Calif. The preparation of the hydroxymethyl resin is described by Bodansky et al., *Chem. Ind.* (London) 38, 1597 (1966). The BHA resin has been described by Pietta and Marshall, *Chem. Comm.*, 650 (1970) and is commercially available from Peninsula Laboratories, Inc., Belmont, Calif.

After the initial attachment, the alpha-amino protecting group can be removed by a choice of acidic reagents, including trifluoroacetic acid (TFA) or hydrochloric acid (HCl) solutions in organic solvents at room temperature. After removal of the alpha-amino protecting group, the remaining protected amino acids can be coupled stepwise in the desired order. Each protected amino acid can be generally reacted in about a 3-fold excess using an appropriate carboxyl group activator such as dicyclohexylcarbodiimide (DCC) or diisopropyl carbodiimide (DIG) in solution, for example, in methylene chloride ($CH_2Cl_2$) or dimethylformamide (DMF) and mixtures thereof.

After the desired amino acid sequence has been completed, the desired peptide can be cleaved from the benzhydrylamine resin support by treatment with a reagent such as hydrogen fluoride (HF) which not only cleaves the peptide from the resin, but also cleaves most commonly used side-chain protecting groups. When a chloromethyl resin or hydroxymethyl resin is used, HF treatment results in the formation of the free peptide acid. However, peptide alkylamides and esters can readily be prepared from these peptide resins by cleavage with a suitable alkylamine, dialkylamine, or diaminoalkane or transesterification with an alcohol at high pH levels.

The solid-phase procedure discussed above is well known in the art and has been described by Stewart and Young, *Solid Phase Peptide Synthesis:* Second Edn. (Pierce Chemical Co., Rockford, Ill. 1984).

Some of the well known solution methods which dan be employed to synthesize the peptide moieties of the instant invention are set forth in Bodansky et al., *Peptide Synthesis*, 2nd Edition, John Wiley & Sons, New York, N.Y. 1976.

It is believed that the peptides will be more preferably synthesized by a solution phase method which involves the condensation reaction of at least two peptide fragments.

This method comprises condensing a peptide fragment X-$A_1$-Y with the peptide fragment U-V-W, wherein all amino acid side-chains except for $A_1$ are neutral or protected, and wherein X is Prot. where Prot. is N-terminus protecting group; Y is $A_2$-Q, Ala-$A_2$-Q, $A_2$-Ala-Q, an Ala-$A_2$-Ala-Q, $A_2$-Ala-Trp-Q, Ala-$A_2$-Ala-Trp-Q, Ala-Q or -Q, where when Y is Q, U is J-$A_2$-Ala-Trp, or J-Ala-$A_2$-Ala-Trp. When Y is Ala-Q, U is J-$A_2$-Ala-Trp. When Y is $A_2$-Q or Ala-$A_2$-Q, U is J-Ala-Trp. When Y is $A_2$-Ala-$_Q$ or Ala-$A_2$-$A_3$-Q, U is J-Trp. When Y is $A_2$-Ala-Trp-Q or Ala-$A_2$-Ala-Trp-Q, U is J. V is $A_5$ or Z. When V is $A_5$, W is Z. When V is Z, W is not present. $A_1$, $A_2$, $A_5$ and Z are as defined herein.

Q is the carboxy terminus of a peptide fragment and is -$OR^3$ or -M, where M is a moiety capable of being displaced by a nitrogen-containing nucleophile and $R^3$ is H, an alkyl group containing one to about 10 carbon atoms, an aryl group having from 6 to about 12 carbon atoms or an arylalkyl group having from 7 to about 12 carbon atoms; J represents the amine terminus of the indicated fragment and is H or a protecting group, which does not hinder the coupling reaction, for example, benzyl.

Thereafter, one removes the protecting groups. Alternatively, one may use the protected peptide thus formed in further condensations to prepare a larger peptide.

This preferred method is more fully described in U.S. patent application Ser. No. 558,121 filed on Jul. 24, 1990, by John C. Hubbs and S. W. Parker entitled "Process for Synthesizing Peptides", published as WO92/01709 which is incorporated herein by reference.

In accordance with another embodiment of the present invention, a method is provided for promoting release and/or elevation of growth hormone levels in the blood of an animal. This method of promoting the release and/or elevation of growth hormone levels can also be used to therapeutically treat the aforesaid diseases. Said methods comprise administering to an animal an effective dose of at least one of the above-described polypeptides. In one embodiment this method is used in animals other than humans.

The compounds of this invention can be administered by oral, parenteral (intramuscular (i.m.), intraperitoneal (i.p.), intravenous (i.v.) or subcutaneous (s.c.) injection), nasal, vaginal, rectal or sublingual routes of administration as well as intrapulmonary inhalation and can be formulated in dose forms appropriate for each route of administration. Parenteral administration is preferred.

Solid dose forms for oral administration include capsules, tablets, pills, powders and granules. In such solid dose forms, the active compound is mixed with at least one inert carrier such as sucrose, lactose, or starch. Such dose forms can also comprise, as is normal practice, additional substances other than inert diluents, e.g., lubricating agents such as magnesium stearate. In the case of capsules, tablets and pills, the dose forms may also comprise buffering agents. Tablets and pills can additionally be prepared with enteric coatings.

Liquid dose forms for oral administration include emulsions, solutions, suspensions, syrups, the elixirs containing inert diluents commonly used in the art, such as water. Besides, such inert diluents, compositions can also include adjuvants, such as wetting agents, emulsifying and suspending agents, and sweetening, flavoring, and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dose forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured in a medium of sterile water, or some other sterile injectable medium immediately before use.

The novel compounds of the present invention are also useful when administered in combination with growth hormone releasing hormone (i.e., naturally occurring growth hormone releasing hormone, analogs and functional equivalents thereof), as well as in combination with other compounds which promote the release of growth hormone, e.g., growth hormone releasing peptides (see U.S. Pat. No. 4,880,778 which is incorporated herein by reference). Such Combinations represent an especially preferred means to administer the growth hormone releasing peptides of the present invention because the combination promotes the release of much more growth hormone than is predicted by the summation of the individual responses for each component of the combination, i.e., the combination provides a synergistic response relative to the individual component. Further details on the administration of combinations of growth hormone releasing peptides are described in the above-cited patent. Such synergistic compounds are preferably compounds which act as an agonist at the growth hormone releasing hormone receptor or inhibit the effect of somatostatin. The synergism can be binary, i.e. the present compound and one of the synergistic compounds, or involve more than one synergistic compound.

Combinations effective to cause the release and elevation of the level of growth hormone in the blood of an animal such as humans comprise an effective amount of polypeptides selected from the presently claimed polypeptides and at least one of the following groups: Group 1 polypeptides, or Group 2 polypeptides, wherein Group 1 polypeptides are selected from any of the naturally occurring growth hormone releasing hormones and functional equivalents thereof, wherein said polypeptides act at the growth hormone releasing hormone receptor of mammals and other vertebrates, and crustaceans;

Group 2 polypeptides are selected from any of the polypeptides having the structure:

Tyr-DArg-Phe-NH$_2$;

Tyr-DAla-Phe-NH$_2$;

Tyr-DArg (NO$_2$)-Phe-NH$_2$;

Tyr-DMet (O)-Phe-NH$_2$;

Tyr-DAla-Phe-Gly-NH$_2$

Tyr-DArg-Phe-Gly-NH$_2$;

Tyr-DThr-Phe-Gly-NH$_2$;

Phe-DArg-Phe-Gly-NH$_2$;

Tyr-DArg-Phe-Sar-NH$_2$;

Tyr-DAla-Gly-Phe-NH$_2$;

Tyr-DArg-Gly-Trp-NH$_2$;

Tyr-DArg(NO$_2$)-Phe-Gly-NH$_2$;

Tyr-DMet (O)-Phe-Gly-NH$_2$ (NMe)Tyr-DArg-Phe-Sar-NH$_2$;

Tyr-DArg-Phe-Gly-ol;

Tyr-DArg-Gly-(NMe)Phe-NH$_2$;

Tyr-DArg-Phe-Sar-ol

Tyr-DAla-Phe-Sar-ol

Tyr-DAla-Phe-Gly-Tyr-NH$_2$;

Tyr-DAla-(NMe)Phe-Gly-Met(O)-ol;

Tyr-DArg-(NMe)Phe-Gly-Met(O)-ol;

Gly-Tyr-DArg-Phe-Gly-NH$_2$;

Tyr-DThr-Gly-Phe-Thz-NH$_2$;

Gly-Tyr-DAla-Phe-Gly-NH$_2$;

Tyr-DAla-Phe-Gly-ol;

Tyr-DAla-Gly-(NMe)Phe-Gly-ol;

Tyr-DArg-Phe-Sar-NH$_2$;

Tyr-DAla-Phe-Sar-NH$_2$;

Tyr-DAla-Gly-(NMe)Phe-NH$_2$;

Sar-Tyr-DArg-Phe-Sar-NH$_2$;

Tyr-DCys-Phe-Gly-DCys-NH$_2$ (cylic disulfide);

Tyr-DCys-Phe-Gly-DCys-NH$_2$ (free dithiol);

Tyr-DCys-Gly-Phe-DCys-NH$_2$ (cyclic disulfide);

Tyr-DCys-Gly-Phe-DCys-NH$_2$ (free dithiol);

Tyr-DAla-Phe-Gly-Tyr-Pro-Ser-NH$_2$;

Tyr-DAla-Phe-Sar-Tyr-Pro-Ser-NH$_2$;

Tyr-DAla-Phe-Sar-Phe-Pro-Ser-NH$_2$;

Tyr-DAla-Phe-Gly-Tyr-Hyp-Ser-NH$_2$;

Tyr-DAla-Phe-Sar-Tyr-Hyp-Ser-NH$_2$;

Tyr-DAla-Phe-Sar-Phe-Hyp-Ser-NH$_2$;

Tyr-DArg-Phe-Gly-Tyr-Hyp-Ser-NH$_2$;

Tyr-DArg-Phe-Sar-Tyr-Pro-Ser-NH$_2$;

Tyr-DArg-Phe-Sar-Tyr-Hyp-Ser-NH$_2$;

Tyr-DArg-Phe-Gly-Tyr-Pro-Ser-NH$_2$; and organic or inorganic addition salts of said polypeptides of Group 2; wherein said combination is administered in a ratio such that said combination is effective to cause the synergistic release and elevation of growth hormone in the blood of such animal.

In one preferred embodiment one uses Group 1 and Group 2 compounds along with the present peptides.

The amount of polypeptide or combination of polypeptides of the present invention administered will vary depending on numerous factors, e.g., the particular animal treated, its age and sex, the desired therapeutic affect, the route of administration and which polypeptide or combination of polypeptides are employed. In all instances, however, a dose effective (therapeutically effective amount) to promote release and elevation of growth hormone level in the blood of the recipient animal is used. Ordinarily, this dose level falls in the range of between about 0.1 μg to 10 mg of total polypeptide per kg of body weight. The preferred amount can readily be determined empirically by the skilled artisan based upon the present disclosure.

For example, in humans when the mode of administration is i.v. the preferred dose level falls in the range of about 0.1 μg to 10 μg of total polypeptide per kg of body weight, more preferably, about 0.5 μg to 5 μg of total polypeptide per kg of body weight, still more preferably about 0.7 μg about 3.0 μg per kg of body weight. When combinations of growth hormone releasing peptides are used, lower amounts of the presently described peptide can be used. For example, combining the presently described peptide with, for example, a synergistic compound in Group I of U.S. Pat. No. 4,880,778 such as GHRH, a preferred range is about 0.1 μg to about 5 μg of the presently described compound per kg of body weight and about 0.5 μg to about 15.0 μg of synergistic compound (e.g. GHRH) and more preferably about 0.1 μg to about 3 μg of the present compound with about 1.0 μg to about 3.0 μg of the synergistic compound per kg of body weight.

When the mode of administration is oral, greater amounts are typically needed. For example, in humans for oral administration, the dose level is typically about 30 μg to about 1200 μg of polypeptide per kg of body weight, more preferably about 70 μg to about 600 μg of polypeptide per kg of body weight, still more preferably, about 200 μg to about 600 μg of total polypeptide per kg of body weight. Cows and pigs require about the same dose level as humans, while rats typically require higher dose levels. The exact level can readily be determined empirically based upon the present disclosure.

In general, as aforesaid, the administration of combinations of growth hormone releasing peptides will allow for lower doses of the individual growth hormone releasing compounds to be employed relative to the dose levels required for individual growth hormone releasing compounds in order to obtain a similar response, due to the synergistic effect of the combination.

Also included within the scope of the present invention are compositions comprising, as an active ingredient, the organic and inorganic addition salts of the above-described polypeptides and combinations thereof; optionally, in association with a carrier, diluent, slow release matrix, or coating.

The organic or inorganic addition salts of the growth hormone releasing compounds and combinations thereof contemplated to be within the scope of the present invention include salts of such organic moieties as acetate, trifluoroacetate, oxalate, valerate, oleate, laurate, benzoate, lactate, rosylate, citrate, maleate, fumarate, succinate, tartrate, naphthalate, and the like; and such inorganic moieties as Group I (i.e., alkali metal salts), Group II (i.e. alkaline earth metal salts) ammonium and protamine salts, zinc, iron, and the like with counterions such as chloride, bromide, sulfate, phosphate and the like, as well as the organic moieties referred to above.

Pharmaceutically acceptable salts are preferred when administration to human subjects is contemplated. Such salts include the non-toxic alkali metal, alkaline earth metal and ammonium salts commonly used in the pharmaceutical industry including sodium, potassium, lithium, calcium, magnesium, barium, ammonium and protamine salts which are prepared by methods well known in the art. The term also includes non-toxic acid addition salts which are generally prepared by reacting the compounds of this invention with a suitable organic or inorganic acid. Representative salts include hydrochloride, hydrobromide, sulfate, bisulfate, acetate, oxalate, valerate, oleate, laurate, borate, benzoate, lactate, phosphate, tosylate, citrate, maleate, fumarate, succinate, tartrate, napthylate, and the like.

The invention will be further illustrated by the following non-limiting examples.

EXAMPLE 1

Synthesis of The Growth Hormone Releasing Peptides

Paramethyl benzhydrylamine hydrochloride (pMe-BHA.HCl) resin is placed in a reaction vessel on a commercially available automated peptide synthesizer. The resin is substituted with free amine up to a loading of about 5 mmoles per gram. The compounds are prepared by coupling individual amino acids starting at the carboxy terminus of the peptide sequence using an appropriate activating agent, such as N,N'-dicyclohexylcarbodiimide (DCC). The alpha amine of individual amino acids are protected, for example, as the t-butyloxycarbonyl derivative (t-Boc) and the reactive side chain functionalities are protected as outlined in Table 1.

TABLE 1

Side Chain Protecting Groups Suitable For
Solid Phase Peptide Synthesis

| Arginine: | $N^g$-Tosyl |
|---|---|
| Aspartic Acid: | O-Benzyl |
| Cysteine: | S-para-Methylbenzyl |
| Glutamic Acid: | O-Benzyl |
| Histidine: | $N^{im}$-Tosyl |
| Lysine: | $N^\epsilon$-2,4-Dichlorobenzyloxycarbonyl |
| Methionine: | S-Sulfoxide |
| Serine: | O-Benzyl |
| Threonine: | O-Benzyl |
| Tryptophan: | $N^{in}$-Formyl |
| Tyrosine: | O-2,6-Dichlorobenzyl |

Prior to incorporation of the initial amino acid, the resin is agitated three times (about one minute each) with dichloromethane ($CH_2Cl_2$; about 10 mL/gm of resin), neutralized with three agitations (about two minutes each) of N,N-diisopropylethylamine (DIEA) in dichloromethane (10:90; about 10 mL/gm of resin) and agitated three times (about one minute each) with dichloromethane (about 10 mL/gm of resin). The initial and each of the subsequent amino acids are coupled to the resin using a preformed symmetrical anhydride using about 6.0 times the total amount of the reaction capacity of the resin of a suitably protected amino acid and about 2.0 times the total amount of the binding capacity of the resin of DIG in an appropriate amount of dichloromethane. For amino acids with a low dichloromethane solubility, N,N-dimethylformamide (DMF) is added to achieve a homogenous solution. Generally, the symmetrical anhydride is prepared up to 30 minutes prior to introduction into the reaction vessel at room temperature or below. The dicyclohexylurea that forms upon preparation of the symmetrical anhydride is removed via gravity filtration of the solution into the reaction vessel. Progress of the coupling of the amino acid to the resin is commonly monitored via a color test using a reagent such as ninhydrin (which reacts with primary and secondary amines). Upon complete coupling of the protected amino acid to the resin (>99%), the alpha amine protecting group is removed by treatment with acidic reagent(s). A commonly used reagent consists of a solution of trifluoroacetic acid (TFA) in dichloromethane (33:66).

After the desired amino acid sequence has been completed, the desired peptide can be cleaved from the resin support by treatment with a reagent such as hydrogen fluoride (HF) which not only cleaves the peptide from the resin, but also cleaves most commonly used side-chain protecting groups. When the BHA or p-Me-BHA resin is used, HF treatment results directly in free peptide amides. When a amino acid-Merrifield resin is used, free peptide alkylamides are cleaved by treatment with an appropriate amine (in this case, use of Boc-$N^\epsilon$-FMOC-Lys would allow simultaneous removal of the FMOC group). The complete procedure for incorporation of each individual amino acid residue onto the resin is outlined in Table 2.

TABLE 2

Procedure for Incorporation Of Individual
Amino Acids Onto a Resin

| Reagent | Agitations | Time/Agitation |
|---|---|---|
| 1. Dichloromethane | 3 | 1 min. |
| 2. TFA-Dichloromethane (33:66) | 1 | 2 min. |
| 3. TFA-Dichloromethane (33:66) | 1 | 20 min. |
| 4. Dichloromethane | 3 | 1 min. |
| 5. DIEA, DMF (10:90) | 2 | 2 min |
| 6. Dichloromethane | 3 | 1 min. |
| 7. Boc amino acid/DIC | 1 | 15–120 min.* |
| 8. Dichloromethane | 3 | 1 min. |
| 10. Monitor progress of the coupling reaction** | | |
| 11. Repeat steps 1–12 for each individual amino acid | | |

*Coupling time depends upon the individual amino acid.
**The extent of coupling can be generally monitored by a color test. If the coupling is incomplete, the same amino acid can be recoupled by a different protocol, eg HOBt active ester. If the coupling is complete the next amino acid can then be coupled.

Using this procedure the compounds described in Tables 3 and 4 were made.

EXAMPLE 2

In Vivo GH Release In Rats

Immature female Sprague-Dawley rats were obtained from the Charles River Laboratories (Wilmington, Ma.).

After arrival they were housed at 25° C. with a 14:10 hour light:dark cycle. Water and Purina rat chow were available ad libitum. Pups were kept with their mothers until 21 days of age.

Twenty-six day old rats, six rats per treatment group, were anesthetized interperitoneally with 50 mg/kg of pentobarbital 20 minutes prior to i.v. treatment with peptide. Normal saline with 0.1% gelatin was the vehicle for intravenous (i.v.) injections of the peptides. The anesthetized rats, weighing 55–65 grams, were injected i.v. with the quantity of growth hormone releasing compounds indicated in Table 3. Injection was made as a 0.1 mL solution into the jugular vein.

All animals were sacrificed by guillotine 10 minutes after the final test injection (see Table 3). Trunk blood for the determination of blood GH levels was collected following decapitation. After allowing the blood to clot, it was centrifuged and the serum was separated from the clot. Serum was kept frozen until the day of sampling for radioimmunoassay (RIA) determination of growth hormone levels according to the following procedure, as developed by the National Institute of Arthritis, Diabetes and Digestive and Kidney Diseases (NIADDK).

Reagents are generally added to the RIA analysis tubes at a single sitting, at refrigerator temperature (about 4° C.) in the following sequence:

(a) buffer, (b) "cold" (i.e., non-radioactive) standard or unknown serum sample to be analyzed, (c) radio-iodinated growth hormone antigen, and (d) growth hormone antiserum.

Reagent addition is generally carried out so that there is achieved a final RIA tube dilution of about 1:30,000 (antiserum to total liquid volume; vol:vol).

The mixed reagents are then typically incubated at room temperature (about 25° C.) for about 24 hours prior to addition of a second antibody (e.g., goat or rabbit anti-monkey gamma globulin serum) which binds to and causes precipitation of the complexed growth hormone antiserum. Precipitated contents of the RIA tubes are then analyzed for the number of counts in a specified period of time in a gamma scintillation counter. A standard curve is prepared by plotting number of radioactive counts versus growth hormone (GH) level. GH levels of unknowns are then determined by reference to the standard curve.

Serum GH was measured by RIA with reagents provided by the National Hormone and Pituitary Program.

Serum levels in Table 3 are recorded in ng/mL in terms of the rat GH standard of 0.61 International Units/mg (IU/mg). Data is recorded as the mean+/– standard error of the mean (SEM). Statistical analysis was performed with Student's t-test. In Table 3 the results shown are the average of studies with six rats.

TABLE 3

In Vivo GH Release Prompted By Growth Hormone Releasing Compounds In Pentobarbital Anesthetized Rats (Animals Sacrificed 10 Minutes After Final Injection)

| Column A<br>GH Releasing<br>Peptide | Total<br>Dose[a]<br>(μg/iv) | Control Serum<br>GH ng/ml +<br>SEM (N = 6) | GH Released<br>Serum GH ng/ml +<br>SEM (N = 6) |
|---|---|---|---|
| Ala—His-DβNal—<br>Ala—Trp-DPhe—Lys—NH$_2$[b] | .1 | 337 ± 51 | 610 ± 90 |
|  | .3 | 337 ± 51 | 1140 ± 187 |
|  | 1.0 | 337 ± 51 | 2909 ± 257 |
|  | 3.0 | 337 ± 51 | 3686 ± 436 |
| His-DTrp—Ala—Trp-<br>DPhe—Lys—NH$_2$[b] | .1 | 131 ± 43 | 540 ± 148 |
|  | .3 | 131 ± 43 | 751 ± 88 |
|  | 1.0 | 131 ± 43 | 1790 ± 252 |
|  | 3.0 | 131 ± 43 | 2481 ± 209 |
| DAla-DβNal—Ala—<br>Trp-DPhe—Lys—NH$_2$ | .1 | 337 ± 51 | 1381 ± 222 |
|  | .3 | 337 ± 51 | 2831 ± 304 |
|  | 1.0 | 337 ± 51 | 2886 ± 179 |
|  | 3.0 | 337 ± 51 | 3678 ± 287 |
| Ala-DβNal—Ala—<br>Trp-DPhe—Lys—NH$_2$ | 0.3 | 167 ± 46 | 363 ± 73 |
|  | 1.0 | 167 ± 46 | 1450 ± 294 |
|  | 3.0 | 167 ± 46 | 2072 ± 208 |
|  | 10.0 | 167 ± 46 | 2698 ± 369 |
| DAla-LβNal—Ala—<br>Trp-DPhe—Lys—NH$_2$ | .1 |  | 263 ± 45 |
|  | .3 | 160 ± 151 | 315 ± 85 |
|  | 1.0 | 160 ± 151 | 426 ± 41 |
| DAla-DTrp—Ala—Trp-<br>DPhe—Lys—NH$_2$ | .1 | 111 ± 24 | 526 ± 86 |
|  | .3 | 111 ± 24 | 1608 ± 204 |
|  | 1.0 | 111 ± 24 | 2820 ± 346 |
|  | 3.0 | 111 ± 24 | 2437 ± 214 |
| Ala-DβNal—Ala—<br>NMeTrp-DPhe—Lys—NH$_2$ | .1 | 167 ± 46 | 144 ± 20 |
|  | 0.3 | 167 ± 46 | 258 ± 28 |
|  | 1.0 | 167 ± 46 | 261 ± 24 |
|  | 3.0 | 167 ± 46 | 277 ± 85 |
| D-Leu-DβNal—<br>Ala—Trp-DPhe—Lys—NH$_2$ | .1 | 160 ± 51 | 256 ± 94 |
|  | .3 | 160 ± 51 | 452 ± 49 |
|  | 1.0 | 160 ± 51 | 355 ± 94 |
| D-Trp-DβNal—Ala—<br>Trp-DPhe—Lys—NH 2 | .1 | 160 ± 51 | 226 ± 61 |
|  | .3 | 160 ± 51 | 245 ± 27 |
|  | 1.0 | 160 ± 51 | 437 ± 62 |
| Ala—His-DβNal—Ala-<br>Trp-DPhe—Lys—NH$_2$ | .3 | 160 ± 51 | 1418 ± 302 |
|  | 1.0 | 160 ± 51 | 2201 ± 269 |

TABLE 3-continued

In Vivo GH Release Prompted By Growth
Hormone Releasing Compounds In Pentobarbital Anesthetized Rats
(Animals Sacrificed 10 Minutes After Final Injection)

| Column A GH Releasing Peptide | Total Dose[a] (μg/iv) | Control Serum GH ng/ml + SEM (N = 6) | GH Released Serum GH ng/ml + SEM (N = 6) |
|---|---|---|---|
| His-DTrp-Ala—Trp DPhe—Lys—NH$_2$[b] | .1 | 140 ± 10 | 200 ± 40 |
|  | .3 | 140 ± 10 | 505 ± 50 |
|  | 1.0 | 140 ± 10 | 1640 ± 215 |
| DAsn-DβNal—Ala— Trp-DPhe—Lys—NH$_2$ | .1 | 228 ± 23 | 122 ± 38 |
|  | .3 | 228 ± 23 | 195 ± 21 |
|  | 1.0 | 228 ± 23 | 197 ± 47 |
| DHis-DβNal—Ala— Trp-DPhe—Lys—NH$_2$ | .1 | 228 ± 23 | 386 ± 81 |
|  | .3 | 228 ± 23 | 605 ± 82 |
|  | 1.0 | 228 ± 23 | 930 ± 96 |
| DLys-DβNal—Ala— Trp-DPhe—Lys—NH$_2$ | .1 | 228 ± 23 | 262 ± 31 |
|  | .3 | 228 ± 23 | 340 ± 86 |
|  | 1.0 | 228 ± 23 | 335 ± 56 |
| DSer-DβNal—Ala— Trp-DPhe—Lys—NH$_2$ | .1 | 228 ± 23 | 226 ± 11 |
|  | .3 | 228 ± 23 | 171 ± 48 |
|  | 1.0 | 228 ± 23 | 212 ± 43 |
| Ala—His-DβNal—Ala— Trp-DPhe—Lys—NH$_2$ | .3 | 228 ± 23 | 1746 ± 318 |
|  | 1.0 | 228 ± 23 | 2610 ± 176 |
| Gly-DβNal—Ala—Trp- DPhe—Lys—NH$_2$ | .3 | 160 ± 36 | 1237 ± 249 |
|  | 1.0 | 160 ± 36 | 2325 ± 46 |
|  | 3.0 | 160 ± 36 | 2694 ± 370 |
|  | 10.0 | 160 ± 36 | 3454 ± 159 |
| Ser-DβNal—Ala— Trp-DPhe—Lys—NH$_2$ | .3 | 160 ± 36 | 227 ± 39 |
|  | 1.0 | 160 ± 36 | 595 ± 112 |
|  | 3.0 | 160 ± 36 | 1303 ± 281 |
|  | 10.0 | 160 ± 36 | 2919 ± 320 |
| Met-DβNal—Ala— Trp-DPhe—Lys—NH$_2$ | .3 | 160 ± 36 | 181 ± 48 |
|  | 1.0 | 160 ± 36 | 226 ± 58 |
|  | 3.0 | 160 ± 36 | 316 ± 66 |
|  | 10.0 | 160 ± 36 | 1010 ± 236 |
| Ala—His-DβNal—Ala— Trp-DPhe—Lys—NH$_2$[b] | 0.1 | 160 ± 36 | 822 ± 243 |
|  | 0.3 | 160 ± 36 | 1594 ± 292 |
|  | 1.0 | 160 ± 36 | 2180 ± 284 |
| Gln-DβNal—Ala—Trp- DPhe—Lys—NH$_2$ | 0.3 | 131 ± 43 | 124 ± 15 |
|  | 1.0 | 131 ± 43 | 340 ± 66 |
|  | 3.0 | 131 ± 43 | 476 ± 109 |
|  | 10.0 | 131 ± 43 | 673 ± 228 |
| Pro-DβNal—Ala—Trp- DPhe—Lys—NH$_2$ | 0.3 | 135 ± 32 | 264 ± 31 |
|  | 1.0 | 135 ± 32 | 513 ± 123 |
|  | 3.0 | 135 ± 32 | 1690 ± 103 |
| Gly-DβNal—Ala—Trp- DPhe—Lys—NH$_2$ | 0.3 | 215 ± 33 | 1301 ± 260 |
|  | 1.0 | 215 ± 33 | 2211 ± 146 |
|  | 3.0 | 215 ± 33 | 2364 ± 365 |
| NαAcetyl-Gly- DβNal—Ala—Trp-DPhe— Lys—NH$_2$ | 0.3 | 262 ± 53* | 268 ± 21* |
|  | 1.0 | 262 ± 53* | 599 ± 219* |
|  | 3.0 | 262 ± 53* | 626 ± 210* |
| Sar-DβNal—Ala—Trp- DPhe—Lys—NH$_2$ | 0.3 | 262 ± 53* | 908 ± 264* |
|  | 1.0 | 262 ± 53* | 1681 ± 262* |
|  | 3.0 | 262 ± 53* | 2600 ± 316* |
| DβNal—Ala—Trp-DPhe— Lys—NH$_2$ | 0.3 | 215 ± 33 | 436 ± 98 |
|  | 1.0 | 215 ± 33 | 660 ± 151 |
|  | 3.0 | 215 ± 33 | 776 ± 274 |
| NαAcetyl-DβNal—Ala— Trp-DPhe—Lys—NH$_2$ | 0.3 | 262 ± 53* | 339 ± 17* |
|  | 1.0 | 262 ± 53* | 430 ± 136* |
|  | 3.0 | 262 ± 53* | 634 ± 118* |
| NαIsopropyl-DβNal—Ala— Trp-DPhe—Lys—NH$_2$ | 0.3 | 262 ± 53* | 541 ± 179* |
|  | 1.0 | 262 ± 53* | 972 ± 247* |
|  | 3.0 | 262 ± 53* | 1636 ± 371* |
| Nαdiethyl-DβNal—Ala— Trp-DPhe—Lys—NH$_2$ | 0.3 | 127 ± 32* | 462 ± 132* |
|  | 1.0 | 127 ± 32* | 899 ± 160* |
|  | 3.0 | 127 ± 32* | 1786 ± 373* |
| Nαethyl-DβNal—Ala— Trp-DPhe—Lys—NH$_2$ | 0.3 | 135 ± 32 | 531 ± 80 |
|  | 1.0 | 135 ± 32 | 1156 ± 250 |
|  | 3.0 | 135 ± 32 | 2664 ± 225 |
| Gly-DβNal—Ala—Trp- DPhe—Lys—NH$_2$ | 0.3 | 135 ± 32 | 1387 ± 352 |
|  | 1.0 | 135 ± 32 | 1958 ± 353 |
|  | 3.0 | 135 ± 32 | 2605 ± 97 |
| βAla-DβNal—Ala—Trp- DPhe—Lys—NH$_2$ | 0.3 | 135 ± 32 | 1937 ± 343 |
|  | 1.0 | 135 ± 32 | 3603 ± 645 |
|  | 3.0 | 135 ± 32 | 4000 ± 500 |
| Ava**-DβNal—Ala— Trp-DPhe—Lys—NH$_2$ | 0.3 | 135 ± 32 | 2469 ± 185 |
|  | 1.0 | 135 ± 32 | 4034 ± 680 |

TABLE 3-continued

In Vivo GH Release Prompted By Growth
Hormone Releasing Compounds In Pentobarbital Anesthetized Rats
(Animals Sacrificed 10 Minutes After Final Injection)

| Column A<br>GH Releasing<br>Peptide | Total<br>Dose[a]<br>(μg/iv) | Control Serum<br>GH ng/ml +<br>SEM (N = 6) | GH Released<br>Serum GH ng/ml +<br>SEM (N = 6) |
|---|---|---|---|
| | 3.0 | 135 ± 32 | 3142 ± 392 |
| Ala-DβNal—Ala—Trp-<br>DPhe—NHCH$_2$CH$_2$NH$_2$ | 0.3 | 208 ± 148* | 211 ± 27* |
| | 1.0 | 208 ± 148* | 468 ± 127* |
| | 3.0 | 208 ± 148* | 877 ± 325* |
| | 30.0 | 208 ± 148* | 2325 ± 477* |
| Ala-DβNal—Ala—Trp-DPhe—<br>NHCH$_2$CH$_2$CH$_2$CH$_2$CHNH$_2$ | 0.3 | 208 ± 148* | 284 ± 132* |
| | 1.0 | 208 ± 148* | 527 ± 166* |
| | 3.0 | 208 ± 148* | 816 ± 289* |
| | 30.0 | 208 ± 148* | 3650 ± 772* |
| D-Ala-DβNal—Ala—Trp-DPhe—<br>NHCH$_2$CH$_2$CH$_2$CH$_2$CH$_2$NH$_2$ | 0.3 | 111 ± 24 | 180 ± 37 |
| | 1.0 | 111 ± 24 | 686 ± 135 |
| | 3.0 | 111 ± 24 | 1490 ± 179 |
| | 10.0 | 111 ± 24 | 2248 ± 70 |
| Ala-DβNal—Ala—Trp-<br>DPhe—OMe | 0.3 | 208 ± 148* | 211 ± 48* |
| | 1.0 | 208 ± 148* | 157 ± 35* |
| | 3.0 | 208 ± 148* | 492 ± 147* |
| | 30.0 | 208 ± 148* | 554 ± 127* |
| D-Ala-DTrp—Ala—<br>Trp-DPhe—Lys—NH$_2$ | 0.1 | 111 ± 24 | 526 ± 86 |
| | 0.3 | 111 ± 24 | 1608 ± 204 |
| | 1.0 | 111 ± 24 | 2820 ± 346 |
| | 3.0 | 111 ± 24 | 2437 ± 214 |
| Aib-DβNal—Ala—Trp-<br>DPhe—Lys—NH$_2$ | 0.1 | 208 ± 148* | 269 ± 58* |
| | 0.3 | 208 ± 148* | 331 ± 108* |
| | 1.0 | 208 ± 148* | 368 ± 133* |
| | 3.0 | 208 ± 148* | 1090 ± 176* |
| D-Ala-DβNal—Ala—Trp—DPhe—<br>Lys(ζ1Pr)—NH$_2$ | 0.1 | 215 ± 49 | 608 ± 115 |
| | 0.3 | 215 ± 49 | 1753 ± 419 |
| | 1.0 | 215 ± 49 | 1817 ± 297 |
| | 3.0 | 215 ± 49 | 2336 ± 196 |

*Dissolved in DMSO,
**Dissolved in aminovaleric acid (Ava)
[a]Doses so noted were administered to 29 day old female rats.
[b]Control GHRP's In Table 3, compounds of the invention are compared to compounds outside of the present generic formula and shown to promote the release and elevation of growth hormone levels in the blood of rats to which such compounds have been administered in a superior fashion. The surprising growth hormone releasing activity of the preferred compounds are quite valuable since a shorter-chain, lower molecular weight polypeptide with the relatively stable and inexpensive amino acid D-alanine at the amino-terminus and pentanediamine in place of Lys at the C-terminus should prove to be a low cost means to enhance growth hormone levels in animals and humans.

EXAMPLE 3 - In Vivo GH Release In Rats After Oral Administration

The procedure of Example 2 was repeated, except the rats were given indicated doses of compounds by intragastric tubes. The compounds administered, the dose levels employed and results are set forth in Table 4.

TABLE 4

In Vivo GH Release Promoted By Growth
Hormone Releasing Compounds In Pentobarbital Anesthetized Rats
(Rats sacrificied at various times after intragastric administration of peptide)

| Column A<br>GH Releasing<br>Peptide | Total<br>Dose<br>(mg/kg) | Serum GH ng/ml ±<br>SEM<br>(N = 6) | Serum GH nb/ml ±<br>SEM (N = 6 at:)<br>15'<br>(20')<br>(30') |
|---|---|---|---|
| Ala—His-DβNal—Ala—<br>Trp-DPhe—Lys—NH$_2$[a] | 10 | 247 ± 32 | 786 ± 244 |
| | 30 | 247 ± 32 | 1914 ± 294 |
| DAla-DβNal—Ala—<br>Trp-DPhe—Lys—NH$_2$ | 10* | 247 ± 32 | 116 ± 298 |
| | 30** | 247 ± 32 | 2038 ± 444 |
| Ava-DβNal—Ala—<br>Trp-DPhe—Lys—NH$_2$ | 30 | 322 ± 145* | 2135 ± 586* |

TABLE 4-continued

In Vivo GH Release Promoted By Growth
Hormone Releasing Compounds In Pentobarbital Anesthetized Rats
(Rats sacrificied at various times after intragastric administration of peptide)

| Column A<br>GH Releasing<br>Peptide | Total<br>Dose<br>(mg/kg) | Serum GH ng/ml ±<br>SEM<br>(N = 6) | Serum GH nb/ml ±<br>SEM (N = 6 at:)<br>15'<br>(20')<br>(30') |
|---|---|---|---|
| Gly-DβNal—Ala—<br>Trp-DPhe—Lys—NH$_2$ | 30 | 247 ± 32 | 1072 ± 137 |
| His-DTrp—Ala—<br>Trp-DPhe—Lys—NH$_2$* | 30 | 247 ± 32 | 1810 ± 437 |
| Ala—His-DβNal—Ala—<br>Trp-DPhe—Lys—NH$_2$* | 10 | 196 ± 49 (15')<br>147 ± 30 (20)<br>133 ± 18 (30') | 1421 ± 363<br>1605 ± 621 (20')<br>752 ± 81 (30') |
| DAla-DβNal—Ala—<br>Trp-DPhe—Lys—NH$_2$ | 10 | 196 ± 49 (15')<br>147 ± 30 (20') | 706 ± 133 (15')<br>1062 ± 254 (20') |
| Gly-DβNal—Ala—<br>Trp-DPhe—Lys—NH$_2$ | 10 | 196 ± 49 (15')<br>147 ± 30 (20') | 957 ± 188 (15')<br>1685 ± 524 (20') |
| His-DTrp—Ala—<br>Trp-DPhe—Lys* | 10 | 196 ± 49 (15')<br>147 ± 30 (20') | 1131 ± 189 (15')<br>686 ± 149 (20') |
| βAla—DβNal—Ala<br>Trp-DPhe—Lys—NH$_2$ | 10 | 196 ± 49 (15')<br>147 ± 30 (20') | 1202 ± 429 (15')<br>1217 ± 239 (20') |
| Ava-DβNal—Ala—<br>Trp-DPhe—Lys—NH$_2$ | 10 | 196 ± 49 (15')<br>147 ± 30 (20') | 1407 ± 204 (15')<br>1251 ± 351 (20') |

*Suspension (light* or heavy**)-acetic acid added.
*Control peptides
The compounds of the present invention retain useful levels of GH releasing activity after oral administration to rats. This is valuable since therapeutic usefulness of the peptides is enhanced by this method of administration.

EXAMPLE 4

Condensation Reaction of Peptide Fragments To Form Peptide

General Procedures

Melting points can be determined using a Thomas Hoover capillary melting point apparatus. Infrared (IR) spectra can be recorded on a Perkin-Elmer Model 137 or a Nicolet Model 5DX spectrophotometer and reported in wave numbers (cm$^{-1}$). Mass spectra (MS) can be obtained using a VG Analytical Ltd. Model ZAB-1F Mass Spectrometer in EI (electron impact), FD (field desorption) or FAB (fast atom bombardment) modes. GCMS can be obtained using a Finnigan 4023 GCMS equipped with a 30 m DB5 capillary column (J & W Scientific) using helium carrier gas. Optical rotations can be measured using an Autopol III polarimeter manufactured by Rudolph Research.

$^1$H NMR spectra can be obtained on a JEOL GX-400 NMR instrument operating at 400 MHz or a JEOL GX-270 NMR instrument operating at 270 MHz. These instruments are capable of a routine digital resolution of less than 0.7 Hz. Chemical shifts are expressed in parts per million relative to internal 3-(trimethylsilyl)-tetradeutero sodium propionate (TSP).

High performance liquid chromatography (HPLC) can be accomplished using a Hitachi system consisting of a L-5000 gradient controller and a 655A pump attached to a Vydac 201TP1010 or 218TP1010 semipreparative column. Combinations of water containing 0.2% trifluoroacetic acid and methanol can be used as the eluting solvent. Typically, compounds of interest will be eluted at a flow rate of six mL per minute with a gradient increasing the organic component at a rate of approximately 1–2% per minute. Compounds are then detected at appropriate wavelengths using an LKB 2140 diode array U.V. detector. Integrations can then be accomplished using Nelson Analytical software (Version 3.6).

Reactions will be carried out under an inert atmosphere of nitrogen or argon unless otherwise specified. Anhydrous tetrahydrofuran (THF, U.V. grade) and dimethylformamide (DMF) can be purchased from Burdick and Jackson and used directly from the bottle.

A. Preparation of Tripeptide Fragment - $_2$HN-Trp-DPhe-Lys(Boc)-NH$_2$

N$^α$-Benzyloxycarbonyl-(N$^ε$-t-butoxycarbonyl)lysine amide, 4.

To a 10° C. solution of carbonyldiimidazole (CDI, 2, 88.24 g, 0.544 mol) and dry tetrahydrofuran (THF, 1500 mL), N$^α$-benzyloxycarbonyl-(N$^ε$-t-butoxycarbonyl)lysine (1, 180 g, 0.474 mol), are slowly added. Gas evolution is observed during this addition. While the N$^ε$-benzyloxycarbonyl-(N$^ε$-t-butoxycarbonyl)lysine imidazolide intermediate, 3, is forming, a saturated solution of ammonia and THF (2000 mL) is prepared (anhyd. NH$_3$ gas is passed through THF at 5°–10° C.). After formation of intermediate 3 is judged to be complete (when gas evolution has ceased, approximately 2 hours), one-half of the THF solution containing 3 is added to the ammonia solution. The remainder of the solution containing 3 is added 30 minutes later. A continuous flow of ammonia gas is maintained throughout the additions and for an additional 45 minutes thereafter. Upon addition of the two solutions containing 3, a white precipitate forms. The reaction is allowed to warm to room temperature and to stir for 15 hours. Solvent is removed from the slurry in vacuo. The residue is slurried in water, and the resulting solid is collected by vacuum filtration.

N$^ε$-t-Butoxycarbonyl-lysine-amide, 5.

A solution of the lysine amide 4 (181.48 g, 0.479 mol) in methanol (MeOH, 1000 mL) is added to a catalyst slurry of 5% Pd/C (5 g) in methanol (250 mL) under argon. Hydrogen is bubbled through the reaction mixture (ca. 15 minutes) and the reaction is then stirred under an atmosphere of hydrogen until HPLC analysis indicates that the reaction is complete (36 hours). The hydrogen atmosphere is then displaced with argon. The reaction solution is clarified through a Celite® pad and solvent is removed in vacuo to provide a solid. $N^\alpha$-Benzyloxycarbonyl-D-phenylalanyl-($N^\varepsilon$-t-butoxtcarbonyl) lysine-amide, 8.

$N^\alpha$-Benzyloxycarbonyl-D-phenylalanine (6, 126.39 g, 0.423 mol) is slowly added to a 10° C. solution of CDI (2, 66.03 g, 0.409 mol) in THF (500 mL). Gas evolution is observed during the addition. When gas evolution ceases, the lysine amide 5 (110.75 g, 0.452 mol) is added as a solution in THF (500 mL). After approximately 48 hours the mixture is filtered to remove solids. The filtrate is concentrated in vacuo.

The resulting residue is taken up in ethyl acetate (EtOAc, 500 mL) and is then washed as follows in a separatory funnel:

1. aq HCl (1 N, 3×500 mL) pH of wash 1, ca. 8; subsequent wash pH's, 1
2. water (500 mL),
3. aq $Na_2CO_3$ (½ saturated, 2×500 mL), is filtered to collect the formed crystalline solids (8),
4. Water (3×500 mL).

The organic layer is dried over $MgSO_4$. After clarification, the solvent is removed in vacuo. The resulting residue can be recrystallized from hot EtOAc to provide a second sample of 8.

D-Phenylalanyl-($N^\varepsilon$-t-butoxycarbonyl)lysine-amide, 9.

A methanolic solution (1500 mL) of amide 8 (120.53 g, 0.229 mol) is added to a catalyst slurry of 5% Pd/C (50 g) in MeOH (200 mL). The argon atmosphere is displaced with hydrogen. When HPLC analysis indicates that the reaction is complete (ca. 4 hours), the hydrogen atmosphere is displaced with argon. The reaction solution is then clarified through a Celite® pad and the filtrate is taken to a residue in vacuo. This dipeptide product can be used directly in the preparation of tripeptide 12.

$N^\alpha$-Benzyloxycarbonyl-tryptophyl-D-phenylalanyl-($N^\varepsilon$-t-butoxycarbonyl)lysine-amide, 12.

A 10° C. solution of $N^\alpha$-benzyloxycarbonyl-tryptophan (10, 67.60 g, 0.200 mol), THF (500 mL), and CDI (2, 33.05 g, 0.204 mol) is stirred until gas evolution ceases. A solution of 9 (40.8 g, 0.103 mol) in THF (ca. 200 mL) is then added to the reaction mixture. The resulting solution is allowed to react for 15 hours while warming to room temperature. The solid which forms is then collected by vacuum filtration. The filtrate is taken to a residue by concentration in vacuo. The resulting residue and solid are recombined and taken up in EtOAc (4000 mL) with slight warming. Upon cooling the solution to room temperature, a solid forms. The solid is collected by vacuum filtration. This solid is recrystallized from hot MeOH to afford purified tripeptide 12. The EtOAc filtrate (from the first crystallization) is washed as follows in a separatory funnel:

1. aq HCl (1 N, 2×500 mL),
2. water (1×500 mL),
3. aq $Na_2CO_3$ (½ saturated, 2×500 mL),
4. aq NaCl (1×500 mL).

The organic layer is dried over $MgSO_4$ and then clarified by vacuum filtration. The solvent of the filtrate is removed in vacuo. The resulting residue is again taken up in EtOAc to afford a dry solid. The solid can be subjected to a hot MeOH recrystallization to afford a second crop of 12 as a white solid.

Tryptophyl-D-phenylalanyl-($N^\varepsilon$-t-butyloxycarbonyl)lysine-amide 13.

A methanolic solution (1500 mL) of tripeptide 12 (64.59 g, 0.091 mol) is added to a catalyst slurry of 5% Pd/C (5 g) and MeOH (250 mL) under an argon atmosphere. An additional volume of MeOH (2250 mL) is added. The argon atmosphere is displaced with hydrogen and allowed to react (ca. 24 hours). Upon completion of the reaction, the hydrogen atmosphere is displaced with argon. The solution is clarified through a Celite® pad and the filtrate is concentrated in vacuo to provide tripeptide 13 as a white solid.

B. Preparation of Tripeptide Fragment-K-DAla-$D^\beta$Nal-Ala-OMe $N^\alpha$-benzyloxycarbonyl-D-Alanyl-D-beta-napthyl alanine methyl ester, 25

A solution of EtOAc (400 mL) and D-beta-napthylalanine methyl ester hydrochloride (22, 0.62 mol) are washed with saturated sodium carbonate (400 mL) and 0.8 N aqueous sodium hydroxide (ca. 500 mL). The resulting aqueous phase is removed (pH 8.5) and the organic phase is sequentially washed with half-saturated aqueous $Na_2CO_3$ (150 mL) and then with water (50 mL). The free base form of 22 is isolated upon concentration of the ethyl acetate layer in vacuo.

Dicyclohexylcarbodiimide (DCC, ca. 95 g, 0.46 mol) is added to a −5° C. (ice-ethanol bath) solution of $N^\alpha$-benzyloxycarbonyl-D-alanine (19, 143.5 g, 0.50 mol), N-hydroxysuccinimide (HONSu, 23, 0.62 mol) and the freshly prepared free base form of 22 (ca. 0.52 mol) in DMF (ca. 3 L). The resulting reaction solution is allowed to stir for 24 hours while warming to room temperature. HPLC analysis should be used to see if the reaction is complete. If it is not, the reaction solution is then cooled to ca. −5° C. and an additional portion of dicyclohexylcarbodiimide (ca. 0.17 mol) is added to the reaction. The reaction mixture is then allowed to stir for an additional 24 hours while warming to room temperature. The mixture is then filtered to remove dicyclohexylurea (DCU). Water (1 L) is added to the filtrate and the resulting solution is concentrated in vacuo. The resulting residue is taken up in aqueous 1N HCl (ca. 1 L until the pH of the aqueous phase reaches a pH of 1). The aqueous phase is then extracted with two portions of ethyl acetate (1 L each). The ethyl acetate layers are discarded. The pH of the aqueous phase is then adjusted by addition of cold 2N sodium hydroxide (500 mL) and sodium hydroxide pellets. During this neutralization, the solution is kept cold by addition of cold ethyl acetate (1 L). When the pH of the aqueous phase reaches approximately 7, copious precipitation of a white solid or oil usually results. This precipitate is collected by vacuum filtration or decantation and washed sequentially with half saturated sodium carbonate (2×1500 mL), water (6×1500 mL) and ethyl acetate (3×1500 mL). The resulting material is dried under high vacuum to constant weight. This material can be hydrolyzed directly without further purification.

$N^\alpha$-Benzyloxycarbonyl-D-alanyl-β-napthyl-D-alanine, 26.

Aqueous sodium hydroxide (192 mL, 0.08 g/mL solution, 0.38 mol) is added to a solution of dipeptide 25 (ca. 0.38 mol), water (360 mL) and MeOH (ca. 6 L). The solution is stirred at room temperature until hydrolysis is complete (ca. 24 hours). The disappearance of the starting peptide is established by HPLC analysis. The solution is concentrated in vacuo to a residue which is dissolved in water (ca. 1 L). The aqueous layer (pH ca. 10) is then extracted with EtOAc (2×500 mL) in a separatory funnel. The ethyl acetate layers are discarded. The resulting aqueous phase is adjusted to a pH of approximately 5 with concentrated HCl at which point precipitation of a white solid or oil usually results. The product is collected and is dried in vacuo.

N$^\alpha$-Benzyloxycarbonyl-D-alanyl-D-beta-napthyl alanyl-alanine methyl ester, 20.

The dipeptide N$^\alpha$-benzyloxycarbonyl-D-alanyl-D-beta-napthyl alanine (26, 0.253 mol) is added to a solution of the HONSu (23, 0.505 mol) in DMF (800 mL) under an atmosphere of argon. To this solution, a mixture of alanine methyl ester hydrochloride (15, 0.303 mol), N-methylmorpholine (16, 0.303 mol) and DMF (200 mL) is added. The resulting solution is cooled to 10° C., at which time dicyclohexylcarbodiimide (24, 0.265 mol) in methylene chloride (273 mL) is added. The reaction is monitored by HPLC while the reaction temperature is maintained at 10° C. until the reaction is complete. If after several days (ca. 4), the reaction has not progressed to completion, an additional charge of 24 (0.080 mol) is added and the reaction mixture is allowed to stir for an additional day at 10° C. The reaction is again monitored by HPLC analysis until complete (typically ca. 5 days). The solids which form during the reaction are collected by vacuum filtration. The filtrate is then concentrated to a residue in vacuo. The resulting residue is taken up in ethyl acetate and extracted with half-saturated aqueous Na$_2$CO$_3$ (2×500 mL). The ethyl acetate phase is dried over MgSO$_4$. The resulting solution is clarified and is concentrated to a residue in vacuo.

A 2N aqueous sodium hydroxide solution (7.5 mL, 15 mmol) is added to a methanol (500 mL) and water solution (200 mL) containing N$^\alpha$-Benzyloxycarbonyl-DAla-D$^\beta$Nal-Ala-OMe (13.7 mmol). After the reaction is allowed to stir overnight at room temperature, HPLC analysis indicates the amount of the starting material remaining. When it is essentially complete (ca. overnight), the resulting solution is concentrated in vacuo to a volume of approximately 200 mL. Water (100 mL) is added and the pH is adjusted to approximately 12 by addition of 2N sodium hydroxide (1 mL). The resulting solution is extracted with ethyl acetate (2×500 mL). The ethyl acetate layers are discarded. The pH of the aqueous phase is then adjusted to approximately 5 by addition of aqueous HCl which usually results in the precipitation of the product. It is important to minimize the volume of the aqueous phase to promote this precipitation. The aqueous phase is decanted away from the product and the product is then rinsed with water (2×50 mL). The isolated product is dried to constant weight in vacuo.

C. Condensation Reaction Of Peptide Fragments To Produce Hexapeptide

The two peptides DAla-D$^\beta$Nal-Ala-OH (33, 2.6 mmol) and Trp-D-Phe-Lys(Boc)-NH$_2$ (13, 2.8 mmol) are dissolved in anhydrous DMF and the resulting solution is concentrated in vacuo. This preliminary concentration is carried out in an attempt to remove any traces of methanol which might be present. The resultant peptide mixture is redissolved in DMF and N-hydroxysuccinimide (5.1 mmol) is then added. The resulting solution is then cooled to a solution temperature of −2° C. and dicyclohexylcarbodiimide (3.4 mmol) is then added as a solution in methylene chloride (3.5 mL). The resulting reaction mixture is allowed to stir at −2° C. solution temperature for a period of three days. HPLC analysis is used to determine if the reaction is essentially completed. After this period of time, if it is not, additional dicyclohexylcarbodiimide can then be added and the resultant reaction mixture allowed to stir for an additional day at −2° C. If, on the following day (for a total of four days) HPLC analysis again indicates incomplete reaction, cooling of the reaction mixture should be terminated. The solution temperature of the reaction can be allowed to slowly rise to room temperature (25° C.) over a period of hours (ca. 8). The resultant reaction mixture is allowed to stir overnight at room temperature. The procedure is repeated until the reaction is complete. Then, water (50 mL) is added and the resulting mixture is allowed to stir for an additional day. The reaction solution is then filtered to remove dicyclohexylurea and the resulting filtrate is concentrated in vacuo to a viscous oil. Ethyl acetate and half-saturated aqueous sodium carbonate (200 mL) are added to the resulting residue. The two-phase mixture is vigorously swirled on a rotary evaporator for approximately one hour. Any solids formed are collected to provide the product by filtration on a scintered glass funnel. The organic phase is washed with water and then dried to constant weight in vacuo to provide the product.

DAla-D-$^{62}$ Nal-Ala-Trp-D-Phe-Lys-NH$_2$, 35.

The hexapeptide Benzyloxycarbonyl-DAla-D-$^\beta$Nal-Ala-Trp-D-Phe-Lys-(Boc)-NH$_2$ (34, 1.02 mmol) is added to a room temperature solution of trifluoroacetic acid (30 mL), dimethylsulfide (14 mL), 1,2 ethanedithiol (7 mL) and anisole (2.2 mL) in methylene chloride (15 mL). The homogeneous reaction mixture is allowed to stir for 15 minutes. After this period of time, anhydrous ether (450 mL) is added to cause precipitation of the crude biologically active peptide product 35. This product is isolated by filtration on a scintered glass funnel or by decantation. The resultant product is dissolved in water and lyophilized. The lyophilized product can be further purified by medium pressure chromatography on a 26×460 mm glass column containing Lichroprep™ RP-18 column packing material (C-18, 25–40 nm, irregular mesh). After injection of the peptide as a solution in water, the column is eluted at a flow rate of 9 mL per minute with a shallow gradient of 0 to 25% methanol for 5–20 hours, and then by a gradient of 25 to 55% methanol over ca. 48 hours. The methanol concentration of the gradient is then increased at a rate of 2% per hour. During the elution, the remainder of the solvent composition is made up of water containing 0.2% trifluoroacetic acid. The product (35) is identified by HPLC and is isolated by concentration of the appropriate elution volumes.

The invention has been described in detail with particular reference to preferred embodiments thereof. However, it will be appreciated that those skilled in the art, upon consideration of this disclosure may make variations and modifications within the spirit and scope of the invention.

We claim:

1. A peptide of the formula

A$_1$-A$_2$-Ala-Trp-DPhe-A$_5$, where

A$_1$ is Gly, DAla, βAla, Met, Pro, Sar, Ava, Aib, a N-lower alkyl aminocarboxylic acid, a N,N-bis-lower alkyl amino-carboxylic acid or a lower alkyl aminocarboxylic acid, wherein the lower alkyl group comprises 2 to about 6 straight-chain carbon atoms;

A$_2$ is DTrp, D$^\beta$Nal, D-4-Y-Phe-or 5-Y-D-Trp, wherein Y is Cl, Br, F or H;

A$_5$ is A$_3$-A$_4$-A$_5'$, A$_3$-A$_5$, A$_4$-A$_5$ or A$_5$, wherein (a) A$_3$ is Ala, Gly, DAla, Pro or desAla;

(b) A$_4$ is Ala, Gly, DAla, Pro, a linear lower alkyl aminocarboxylic acid, or desAla; and (c) A$_5'$ is Lys(ε-R$_1$, R$_2$)-Z, Orn (δ-R$_1$,R$_2$)-Z, NH(CH$_2$)$_x$N(R$_3$,R$_4$), Lys-Z, Orn-Z or Arg-Z; wherein R$_1$ is a linear lower alkyl group or H atom; R$_2$ is a linear lower alkyl group or H atom; but R$_1$ and R$_2$ cannot both be H; R$_3$ is a linear lower alkyl group or H atom; R$_4$ is a linear lower alkyl group or H atom; Z is NH(linear lower alkyl group), N(linear lower alkyl group)$_2$, O-(linear lower alkyl group), NH$_2$ or OH, wherein the linear lower alkyl group is as defined as the lower alkyl group alkyl; x is 2 through 6;
and organic or inorganic addition salts of the above.

2. The peptide according to claim 1, wherein $A_1$ is Gly, or DAla.

3. A peptide of the formula
$A_1$-$A_2$-Ala-Trp-DPhe-$A_5$, wherein
 $A_1$ is DAla;
 $A_2$ is DTrp, D$^\beta$Nal, D-4-Y-Phe-or 5-Y-D-Trp, wherein Y is OH, Cl, Br, F or H;
 $A_5$ is $A_3$-$A_4$-A5', $A_3$-$A_5$ $A_4$-$A_5$ or $A_5$, wherein
  (a) $A_3$ is Ala, Gly, DAla, Pro or desAla;
  (b) $A_4$ is Ala, Gly, DAla, Pro, a linear lower alkyl aminocarboxylic acid, or desAla; and
  (c) $A_{5'}$ is Lys($\epsilon$-$R_1$,$R_2$)-Z, Orn($\delta$-$R_1$,$R_2$)-Z, NH(CH$_2$)$_x$N($R_3$,$R_4$), Lys-Z, Orn-Z or Arg-Z; wherein $R_1$ is a linear lower alkyl group or H atom; $R_2$ is a linear lower alkyl group or H atom; but $R_1$ and $R_2$ cannot both be H; $R_3$ is a linear lower alkyl group or H atom; $R_4$ is a linear lower alkyl group or H atom; Z is NH(linear lower alkyl group), N(linear lower alkyl group)$_2$O-(linear lower alkyl group), NH$_2$ or OH, wherein the linear lower alkyl group is as defined as the lower alkyl group alkyl; x is 2 through about 6;
and organic or inorganic addition salts of the above.

4. The peptide according to claim 1, wherein $A_2$ is DTrp or D$^\beta$Nal.

5. The peptide according to claim 1, wherein $A_2$ is D$^\beta$Nal.

6. The peptide according to claim 1, wherein $A_5$ is $A_3$-$A_4$-$A_{5'}$.

7. The peptide according to claim 1, wherein $A_5$ is $A_3$-$A_{5'}$.

8. The peptide according to claim 1, wherein $A_5$ is $A_4$-$A_{5'}$.

9. The peptide according to claims 1, 2, 3, 4 or 5 wherein $A_5$ is $A_{5'}$.

10. A peptide having the formula
DAla-D$^\beta$Nal-Ala-Trp-DPhe-LysNH$_2$,
DAla-D$^\beta$Nal-Ala-Trp-DPhe-Lys($\xi$iPr)NH$_2$,
DAla-DTrp-Ala-Trp-DPhe-Lys($\xi$iPr)NH$_2$,
DAla-DTrp-Ala-Trp-DPhe-LysNH$_2$,
DAla-D$^\beta$Nal-Ala-Trp-DPhe-NH(CH$_2$)$_5$NH$_2$, or
NH$_2$(CH$_2$)$_5$CO-D$^\beta$Nal-Ala-Trp-DPhe-NH(CH$_2$)$_5$NH$_2$
and organic or inorganic addition salts, thereof.

11. A method of promoting the release of growth hormone levels in an animal comprising administering to the animal an effective amount of at least one of the peptides of claims 3 or 10.

12. The method of claim 11, wherein the animal is a mammal.

13. The method of claim 11, wherein the animal is a human.

14. A pharmaceutical composition for promoting the release of growth hormone levels in animals comprising an effective mount of at least one of the peptides of claims 1, 9, or 10 and a pharmaceutically acceptable carrier or diluent.

15. A method of promoting the release and elevation of blood growth hormone levels by administering the peptide of claim 1 in a synergistic amount with a second compound, wherein the second compound is a compound which acts as an agonist at the growth hormone releasing hormone receptor or inhibits the effect of somatostatin.

16. The pharmaceutical composition of claim 14, which further comprises a second compound which acts as an agonist at the growth hormone releasing hormone receptor or inhibits the effects of somatostatin.

17. A method of promoting the release and elevation of blood growth hormone levels by administering the peptide of claim 1 in a synergistic amount with at least a Group 1 polypeptide or a Group 2 polypeptide, wherein the Group 1 polypeptide is selected from any of the naturally occuring growth hormone releasing hormones and functional equivalents thereof and the Group 2 polypeptide is selected from the group of polypeptides comprising;

Tyr-DArg-Phe-NH$_2$;
Tyr-DAla-Phe-NH$_2$;
Tyr-DArg (NO$_2$)-Phe-NH$_2$;
Tyr-DMet (O)-Phe-NH$_2$;
Tyr-DAla-Phe-Gly-NH$_2$
Tyr-DArg-Phe-Gly-NH$_2$;
Tyr-DThr-Phe-Gly-NH$_2$;
Phe-DArg-Phe-Gly-NH$_2$;
Tyr-DArg-Phe-Sar-NH$_2$;
Tyr-DAla-Gly-Phe-NH$_2$;
Tyr-DArg-Gly-Trp-NH$_2$;
Tyr-DArg(NO$_2$)-Phe-Gly-NH$_2$;
Tyr-DMet (O)-Phe-Gly-NH$_2$
(NMe)Tyr-DArg-Phe-Sar-NH$_2$;
Tyr-DArg-Phe-Gly-ol;
Tyr-DArg-Gly-(NMe)Phe-NH$_2$;
Tyr-DArg-Phe-Sar-ol
Tyr-DAla-Phe-Sar-ol
Tyr-DAla-Phe-Gly-Tyr-NH2;
Tyr-DAla-(NMe)Phe-Gly-Met(O)-ol;
Tyr-DArg-(NMe)Phe-Gly-Met(O)-ol;
Gly-Tyr-DArg-Phe-Gly-NH$_2$;
Tyr-DThr-Gly-Phe-Thz-NH$_2$;
Gly-Tyr-DAla-Phe-Gly-NH$_2$;
Tyr-DAla-Phe-Gly-ol;
Tyr-DAla-Gly-(NMe)Phe-Gly-ol;
Tyr-DArg-Phe-Sar-NH$_2$;
Tyr-DAla-Phe-Sar-NH$_2$;
Tyr-DAla-Gly-(NMe)Phe-NH$_2$;
Sar-Tyr-DArg-Phe-Sar-NH$_2$;
Tyr-DCys-Phe-Gly-DCys-NH$_2$ (cylic disulfide);
Tyr-DCys-Phe-Gly-DCys-NH$_2$ (free dithiol);
Tyr-DCys-Gly-Phe-DCys-NH$_2$ (cyclic disulfide);
Tyr-DCys-Gly-Phe-DCys-NH$_2$ (free dithiol);
Tyr-DAla-Phe-Gly-Tyr-Pro-Ser-NH$_2$;
Tyr-DAla-Phe-Sar-Tyr-Pro-Ser-NH$_2$;
Tyr-DAla-Phe-Sar-Phe-Pro-Ser-NH$_2$;
Tyr-DAla-Phe-Gly-Tyr-Hyp-Ser-NH$_2$;
Tyr-DAla-Phe-Sar-Tyr-Hyp-Ser-NH$_2$;
Tyr-DAla-Phe-Sar-Phe-Hyp-Ser-NH$_2$;
Tyr-DArg-Phe-Gly-Tyr-Hyp-Ser-NH$_2$;
Tyr-DArg-Phe-Sar-Tyr-Pro-Ser-NH$_2$;
Tyr-DArg-Phe-Sar-Tyr-Hyp-Ser-NH$_2$; and
Tyr-DArg-Phe-Gly-Tyr-Pro-Ser-NH$_2$; and
organic or inorganic addition salts, thereof.

18. The method of claim 17, wherein one uses a Group 1 polypeptide and a Group 2 polypeptide.

19. The peptide according to claim 3, wherein $A_2$ is D$^\beta$Nal.

20. The peptide according to claim 3, having the formula Dala-D$^\beta$Nal-Ala-Trp-DPhe-Lys-Z.

21. A peptide having the formula DAla-D$^\beta$Nal-Ala-Trp-DPhe-Lys-NH$_2$ and organic or inorganic addition salts thereof.

22. A method of promoting the release and elevation of growth hormone levels in an animal comprising administering to the animal an effective amount of a peptide having the formula DAla-D$^\beta$Nal-Ala-Trp-DPhe-Lys-Z, wherein Z is NH(linear $C_2$–$C_{10}$ alkyl group), N(linear $C_2$–$C_{10}$ alkyl group)$_2$, O-(linear $C_2$–$C_{10}$ alkyl group), NH$_2$ or OH, and organic or inorganic addition salts thereof.

23. The method of claim 22, wherein the peptide has the formula DAla-D$^\beta$Nal-Ala-Trp-DPhe-Lys-NH$_2$.

24. A pharmaceutical composition comprising an effective amount of a peptide having the formula DAla-D$^\beta$Nal-Ala-Trp-DPhe-Ly-Z and a pharmaceutically acceptable carrier or diluent, wherein Z is NH(linear $C_2$–$C_{10}$ alkyl group), N(linear $C_2$–$C_{10}$ alkyl group)$_2$, O-(linear $C_2$–$C_{10}$ alkyl group), NH$_2$ or OH, and organic or inorganic addition salts thereof.

25. The pharmaceutical composition of claim 24, wherein the peptide has the formula D-Ala-D$^\beta$Nal-Ala-Trp-DPhe-Lys-NH$_2$.

26. A method of promoting the release and elevation of blood growth hormone levels by administering a peptide having the formula DAla-D$^\beta$Nal-Ala-Trp-DPhe-Lys-Z wherein Z is NH(linear $C_2$–$C_{10}$ alkyl group), N(linear $C_2$–$C_{10}$ alkyl group)$_2$, O-(linear $C_2$–$C_{10}$ alkyl group), NH$_2$ or OH, and organic or inorganic addition salts thereof, in a synergistic amount with a second compound, wherein the second compound is a compound which acts as an agonist at the growth hormone releasing hormone receptor or inhibits the effect of somatostatin.

27. The method of claim 26, wherein the peptide has the formula DAla-D$^\beta$Nal-Ala-Trp-DPhe-Lys-NH$_2$.

28. A peptide of the formula $A_1$-$A_2$-Ala-Trp-DPhe-$A_5$, where $A_1$ is Gly, DAla or $\beta$Ala, $A_2$ is DTrp, D$^\beta$Nal, D-4-Y-Phe-or 5-Y-D-Trp, wherein Y is OH, Cl, Br, F or H;

$A_5$ is $A_3$-$A_4$-$A_{5'}$, $A_3$-$A_{5'}$, $A_4$-$A_5$, or $A_{5'}$, wherein (a) $A_3$ is Ala, Gly, DAla, or Pro;

(b) $A_4$ is Ala, Gly, DAla, Pro, or a linear lower alkyl aminocarboxylic acid, and (c) $A_{5'}$ is Lys($\epsilon$-$R_1$, $R_2$)-Z, Orn($\delta$-$R_1$,$R_2$)-Z, NH(CH$_2$)$_x$N($R_3$,$R_4$), Lys-Z, Orn-Z or Arg-Z;

wherein $R_1$ is a linear lower alkyl group or H atom; $R_2$ is a linear lower alkyl group or H atom; but when $R_1$ is H, $R_2$ is not H; and when $R_2$ is H, $R_1$ is not H; $R_3$ is a linear lower alkyl group or H atom; $R_4$ is a linear lower alkyl group or H atom; Z is NH(linear lower alkyl group), N(linear lower alkyl group)$_2$, O-(linear lower alkyl group), NH$_2$ or OH, wherein the linear lower alkyl group; x is 2 through 15;

and organic or inorganic addition salts of the above.

29. The peptide according to claim 28, wherein $A_2$ is DTrp or D$^\beta$Nal.

30. A peptide of the formula $A_1$-D$\beta$Nal-Ala-Trp-DPhe-$A_5$, where $A_1$ is Gly, DAla or $\beta$Ala;

$A_5$ is $A_3$-$A_4$-$A_{5'}$, $A_3$-$A_{5'}$, $A_4$-$A_5$, or $A_{5'}$, wherein (a) $A_3$is Ala, Gly, DAla, or Pro;

(b) $A_4$ is Ala, Gly, DAla, Pro, or a linear lower alkyl aminocarboxylic acid, and (c) $A_{5'}$ is Lys($\epsilon$-$R_1$, $R_2$)-Z, Orn($\delta$-$R_1$,$R_2$)-Z, NH(CH$_2$)-N($R_3$,$R_4$), Lys-Z, Orn-Z or Arg-Z; wherein $R_1$ is a linear lower alkyl group or H atom; $R_2$ is a linear lower alkyl group or H atom; but when $R_1$ is H, $R_2$ is not H; and when $R_2$ is H, $R_1$ is not H; $R_3$ is a linear lower alkyl group or H atom; $R_4$ is a linear lower alkyl group or H atom; Z is NH(linear lower alkyl group), N(linear lower alkyl group)$_2$, O-(linear lower alkyl group), NH$_2$ or OH, wherein the linear lower alkyl group x is 2 through 15; and organic or inorganic addition salts of the above.

31. A peptide of the formula

DAla-$A_2$-Ala-Trp-DPhe-$A_5$, where $A_2$ is DTrp, D$^\beta$Nal, D-4-Y-Phe-or 5-Y-D-Trp, wherein Y is OH, Cl, Br, F or H;

$A_5$ is $A_3$-$A_4$-$A_{5'}$, $A_3$-$A_{5'}$, $A_4$-$A_5$, or $A_{5'}$, wherein (a) $A_3$ is Ala, Gly, DAla, or pro;

(b) $A_4$ is Ala, Gly, DAla, Pro, or a linear lower alkyl aminocarboxylic acid, and (c) $A_{5'}$ is Lys($\epsilon$-$R_1$, $R_2$)-Z, Orn($\delta$-$R_1$,$R_2$)-Z, NH(CH$_2$)$_x$N($R_3$,$R_4$), Lys-Z, Orn-Z or Arg-Z; wherein $R_1$ is a linear lower alkyl group or H atom; $R_2$ is a linear lower alkyl group or H atom; but when $R_1$ is H, $R_2$ is not H; and when $R_2$ is H, $R_1$ is not H; $R_3$ is a linear lower alkyl group or H atom; $R_4$ is a linear lower alkyl group or H atom; Z is NH(linear lower alkyl group), N(linear lower alkyl group)$_2$, O-(linear lower alkyl group), NH$_2$ or OH, wherein the linear lower alkyl group is 2 through about 10 carbon atoms; x is 2 through 15;

and organic or inorganic addition salts of the above.

32. The peptide of claim 31, wherein $A_2$ is D$\beta$Nal.

33. A pharmaceutical composition comprising an effective amount of the peptide of claim 28 in a pharmaceutically acceptable carrier or diluent.

34. A peptide of the formula

DAla-$A_2$-Ala-Trp-DPhe-$A_5$, wherein $A_2$ is DTrp or D$\beta$Nal;

$A_5$ is $A_3$-$A_4$-$A_{5'}$, $A_3$-$A_{5'}$, $A_4$-$A_5$, or $A_{5'}$, wherein (a) $A_3$ is Ala, Gly, DAla, or Pro;

(b) $A_4$ is Ala, Gly, DAla, Pro, or a linear lower alkyl aminocarboxylic acid, and (c) $A_{5'}$ is Lys($\epsilon$-$R_1$, $R_2$)-Z, Orn($\delta$-$R_1$,$R_2$)-Z, NH(CH$_2$)$_x$N($R_3$,$R_4$), Lys-Z, Orn-Z or Arg-Z; wherein $R_1$ is a linear lower alkyl group or H atom; $R_2$ is a linear lower alkyl group or H atom; but when $R_1$ is H, $R_2$ is not H; and when $R_2$ is H, $R_1$ is not H; $R_3$ is a linear lower alkyl group or H atom; $R_4$ is a linear lower alkyl group or H atom; Z is NH(linear lower alkyl group), N(linear lower alkyl group)$_2$, O-(linear lower alkyl group), NH$_2$ or OH, wherein the linear lower alkyl group; x is 2 through 15;

and organic or inorganic addition salts of the above.

35. A pharmaceutical composition comprising an effective amount of the peptide of claim 34 in a pharmaceutically acceptable carrier or diluent.

* * * * *